United States Patent
Hodgson

(10) Patent No.: US 11,241,561 B2
(45) Date of Patent: Feb. 8, 2022

(54) BALLOON CATHETER WITH POROUS OUTER MEMBER FOR AIR PURGING

(71) Applicants: STRYKER CORPORATION, Kalamazoo, MI (US); STRYKER EUROPEAN OPERATIONS LIMITED, Carrigtwohill (IE)

(72) Inventor: Kyler Hodgson, Salt Lake City, UT (US)

(73) Assignee: Stryker Corporation, Kalamazoo, MI (US)

( * ) Notice: Subject to any disclaimer, the term of this patent is extended or adjusted under 35 U.S.C. 154(b) by 187 days.

(21) Appl. No.: 16/690,981

(22) Filed: Nov. 21, 2019

(65) Prior Publication Data

US 2021/0154448 A1    May 27, 2021

(51) Int. Cl.
*A61M 25/10*    (2013.01)
*A61M 5/00*    (2006.01)

(52) U.S. Cl.
CPC ...... *A61M 25/10184* (2013.11); *A61M 5/007* (2013.01); *A61M 2025/1077* (2013.01); *A61M 2025/1086* (2013.01)

(58) Field of Classification Search
CPC ............ A61M 5/007; A61M 25/10184; A61M 2025/1077; A61M 2025/1086
See application file for complete search history.

(56) References Cited

U.S. PATENT DOCUMENTS

| | | | |
|---|---|---|---|
| 5,100,385 A | 3/1992 | Bromander | |
| 6,638,245 B2 | 10/2003 | Miller et al. | |
| 2020/0353228 A1* | 11/2020 | Casey | A61M 25/10184 |

FOREIGN PATENT DOCUMENTS

| | | |
|---|---|---|
| EP | 0284672 | 10/1988 |
| JP | 2005-103120 | 4/2005 |
| WO | 89/07958 | 9/1989 |
| WO | 03/099352 | 12/2003 |

OTHER PUBLICATIONS

PCT International Search Report and Written Opinion for International Appln. No. PCT/US2020/059477, Applicant Stryker Corporation, dated Mar. 12, 2021 (13 pages).

* cited by examiner

*Primary Examiner* — Nathan R Price
*Assistant Examiner* — Melissa A Snyder
(74) *Attorney, Agent, or Firm* — Vista IP Law Group, LLP

(57) ABSTRACT

A balloon catheter which allows for faster preparation and effective purging of air. The catheter includes an elongated, flexible catheter having a tubular outer member and a tubular inner member each having a respective lumen. The inner member is at least partially disposed in the outer member lumen such that an outer surface of the inner member and an inner surface of the outer member together define an annular inflation lumen. The outer member has micropores or micro-holes configured such that when a contrast agent is injected into the inflation lumen, the micropores or micro-holes allow air to pass therethrough and thereafter become clogged by the contrast agent. The catheter also has a balloon member having its ends secured to and circumferentially around the outer member such that an inner surface of the balloon member and the outer surface of the outer member define an inflatable balloon interior.

17 Claims, 11 Drawing Sheets

BALLOON CATHETER WITH POROUS OUTER MEMBER FOR AIR PURGING

FIELD OF THE INVENTION

The disclosed inventions generally relate to medical devices and methods for performing procedures within a lumen of a vascular system of a patient, and more particularly, to a balloon catheter for use within a vascular system, and method of using the same, which is configured to allow for fast and effective purging of unwanted air from balloon catheter.

BACKGROUND

Various designs of medical catheters have been previously provided for performing a variety of medical procedures, including interventional therapy, drug delivery, diagnosis, perfusion, and the like. In general, medical catheters are used by introducing the catheter through an entry site of a patient and into the vascular system of the patient, such as a vein or artery. The catheter is advanced from the entry site by guiding and pushing the catheter through the vascular system to a target site for performing a therapeutic and/or diagnostic medical procedure.

An example of one type of intravascular catheter is a balloon catheter which includes an elongated tubular member, wherein a balloon member is affixed, for example, to a distal end portion of the tubular member or other suitable location to form an inflatable balloon interior between an inner surface of the balloon member and the outer surface of the tubular member. On common type of balloon catheter is a balloon guide catheter which is used to guide other instruments to a desired site within a vascular system. The tubular member includes an inflation lumen extending from a proximal end of the tubular member to the inflatable balloon interior for injecting fluid—to thereby inflate—the balloon. Various types of balloon catheters have been previously disclosed for performing a variety of different medical procedures. For instance, balloon guide catheters used in conjunction with treating neurological disorders, such as ischemic stroke, are disclosed in U.S. Pat. No. 6,638,245 (the '245 patent), the disclosure of which is fully incorporated herein. FIGS. 13A and 13B illustrate a prior art balloon guide catheter 250 as disclosed in the '245 patent (reference numbers have been changed from the '245 patent). The balloon guide catheter 250 comprises an outer tubular member 270 and an inner tubular member 272 within the outer tubular member 270. The balloon guide catheter 250 has an inflatable balloon 260 disposed on the distal end of the outer tubular member 270. The annular space between the outer tubular member 270 and the inner tubular member 272 forms a fluid supply lumen 258 for inflating the balloon 260. The balloon guide catheter 250 is advanced to a target site within the vascular system of a patient through an introducer sheath. Once in place, treatment catheters may be advanced to the target site through the working lumen 252 of the inner tubular member 272. Accordingly, prior balloon guide catheters, such as the balloon guide catheter 250, required at least three catheter shaft thicknesses (the combined thicknesses of the outer tubular member 270, the inner tubular member 272 and the introducer sheath).

The use of balloon catheters in the neurological vasculature presents a number of catheter design challenges. For one, the blood vessels in the brain are typically very small in diameter, as small as several millimeters or less, requiring that a catheter advanced into these blood vessels have an outside diameter as small as one French (0.33 mm). Furthermore, the brain vasculature is highly tortuous, requiring that a neurological catheter be very flexible, especially at the distal end, to travel through and conform to the tortuous path. Also, the blood vessels of the brain are quite fragile, so a neurological catheter must have a smooth, non-traumatic periphery.

Balloon catheters, including balloon guide catheters, generally require preparation prior advancing the balloon catheter into the vasculature of a patient by purging any unwanted air bubbles out of the respective balloon inflation lumen and balloon interior. As described above, a balloon catheter typically has an elongated tube and an inflation lumen. In some cases, a balloon catheter may also have multiple tubes (e.g., concentric tubes with an inner tube disposed within an outer tube). Each of these structures, including the tube(s), inflation lumen, and balloon must be purged of air with a fluid (e.g., saline) prior to advancing the balloon catheter through the vasculature of the patient to prevent air from being introduced into the patient which can cause embolisms or other trauma in the patient.

However, due to the closed-end fluid path from the inflation lumen to the balloon, and in many cases, within the working lumen of the balloon catheter, it is difficult and very time-consuming to purge all of the air from system. It is also difficult to determine when all of the air has been purged because of the closed-end fluid paths. As a result, purging the air from prior balloon catheters during preparation for surgery often takes up to 15 minutes, and even then, the purging is not always successful. However, due to the closed-end fluid path from the inflation lumen to the balloon, and in many cases, within the tube(s) of the catheter, it is difficult and very time-consuming to purge all of the air from system. It is also difficult to determine when all of the air has been purged from the catheter because of the closed-end fluid paths. As a result, purging the air from prior balloon catheters during preparation for surgery often takes up to 15 minutes, and even then, the purging is not always successful.

SUMMARY

The disclosed inventions are directed to balloon catheters having an innovative configuration which allows for fast preparation and effective purging of air within the catheter, including purging air from the balloon inflation lumen and balloon interior. While the description of the disclosed inventions will be directed to balloon guide catheters used for insertion and positioning of therapeutic devices within a vascular system of a patient, it is understood that the disclosed inventions are not limited to balloon guide catheters, but may be used with any suitable balloon catheter.

As explained above, balloon catheters typically require preparation prior to use, including purging air from the system before advancing the catheter into the vasculature of a patient. The balloon catheters of the disclosed inventions are configured to allow fast and effective purging of air from the catheter, in particular, from the balloon inflation lumen and balloon in a single aspiration step, allowing a simpler and faster preparation procedure than with existing balloon catheters.

In an exemplary embodiment of the disclosed inventions, a balloon catheter includes an elongated, flexible, tubular outer member having a proximal portion, a distal portion, and an outer member lumen extending therebetween. The outer member is formed of a microporous material such that the wall of the outer member has micropores. The micropores are configured (e.g., sized) such that the micropores allow air to pass through the wall of the outer member when a contrast agent is injected into the outer member lumen. Air passes from the outer member lumen through the micropores to an exterior of the outer member. Typically, the contrast agent is mixed with saline to form a contrast agent/saline mixture, and therefore, the term "contrast agent" as used herein means contrast agent, contrast agent/saline mixture, or contrast agent mixed with any other fluid. Moreover, the micropores allow air to pass through, and thereafter become clogged by the contrast agent thereby sealing the micropores from allowing contrast agent to pass through the micropores.

The balloon catheter further includes a flexible, elongated tubular inner member having a proximal portion, a distal portion, and an inner member lumen extending therebetween. The inner member lumen is in communication with a distal opening of the inner member. The inner member is at least partially disposed in the outer member lumen such that an outer surface of the inner member and an inner surface of the outer member together define an annular inflation lumen.

The balloon member is secured to the outer member. The balloon member can be secure to any suitable portion of the outer member, including but not limited to the distal portion. The proximal and distal ends of the balloon are secured to and circumferentially around an outer surface of the outer member such that an inner surface of the elastomeric member and an outer surface of the outer member define an inflatable balloon interior.

The outer member also has one or more inflation passages through the wall of the outer member that form a fluid pathway between the annular inflation lumen and the balloon interior. The inflation passages may be holes in the through the wall of the outer member which fluidly connect the annular inflation lumen and the balloon interior.

In various embodiments, the microporous material has micropores having a nominal pore size diameter in the range of from 0.1 µm to 2 µm. This configuration of the microporous material allows air to pass out through the micropores of the outer member when contrast agent is injected into the inflation lumen, and thereafter, the micropores are clogged and sealed by the contrast agent. Further, the pore size diameter of the micropores preferably does not exceed 5 µm, which helps ensure that the micropores can be properly sealed by the contrast agent, without allowing excessive contrast agent to leak out through the micropores.

In various embodiments, the microporous material may be any suitable material for making a flexible, elongated tube to form the outer member, such as any of the following: TYVEK™ 3345, woven polymer, woven plastic, ePTFE, sintered plastic, sintered polymer, and GORETEX™ fabric membrane.

In various embodiments, the micropores may extend from the proximal portion to the distal portion of the outer member. In this way, there are micropores for venting air trapped in the inflation lumen along the entire outer member, which decreases the time required to purge air from the balloon catheter.

In various embodiments, the microporous material has micropores having a nominal pore area size in the range of from 0.079 µm² to 12.5 µm². Similar to the pore size diameter, this feature allows air to pass out through the micropores of the outer member when contrast agent is injected into the inflation lumen, and thereafter, the contrast agent clogs the micropores thereby sealing the micropores from allowing contrast agent to pass through the micropores.

Another aspect of the disclosed inventions is directed to a method of purging air from the above-described exemplary embodiments of the balloon catheter, wherein a contrast agent is injected into the annular inflation lumen and flows through the respective annular inflation lumen, inflation passages, and into the balloon interior, thereby purging air from the inflation lumen and the balloon interior out the micropores of the outer member. A positive pressure of contrast agent is maintained in the annular inflation lumen such that, after the air is purged from the inflation lumen and the balloon interior, the contrast agent seals the micropores of the outer member. To complete the purging of air from the entire balloon catheter, the inner member may be purged by flushing the inner member lumen with a flushing fluid, such as saline, until the unwanted air is removed from the inner member lumen. The balloon catheter is now prepared ("prepped" for use in a surgical procedure). Accordingly, the balloon catheter allows very fast and effective purging of air in the preparation of the balloon catheter for use in performing a surgical procedure.

The preparation method may also include positioning the balloon catheter with the tubular outer member elevated above the balloon such that air trapped in the balloon is forced into the tubular outer member and passes out of the tubular member through the micropores of the outer member.

Preferably, contrast agent is injected into the annular inflation lumen with sufficient pressure to inflate the balloon member. After the air is purged from the inflation lumen and balloon member, the balloon member may be deflated by reducing the pressure of contrast agent.

The preparation method may further include inspecting the balloon for air bubbles while the balloon is inflated with contrast agent (e.g., a user visually inspecting the balloon), and determining that any air bubbles in the balloon are purged from balloon. Then, after determining that any air bubbles in the balloon are purged from balloon, the balloon is deflated by reducing the pressure of the contrast agent within the inflation lumen and balloon interior.

In one exemplary use, the prepared (air-purged) balloon catheter is inserted into the vascular system of the patient. For example, the balloon catheter may be inserted through an entry incision into an entry blood vessel, such as the inferior vena cava or femoral artery near the groin. The inner member and outer member are then advanced through the vascular system to position the balloon at a treatment site. The inner member and outer member may be advanced simultaneously, or separately, and at the same rate or different rates. With the balloon positioned at the treatment site, the balloon member is inflated by injecting contrast agent into the inflation lumen, thereby increasing the pressure of contrast agent in the inflation lumen and balloon member. The balloon may be inflated within the blood vessel such that the balloon seals the blood vessel. This isolates the blood vessel downstream of the balloon from the flow of blood. A treatment procedure, such as imaging, embolus removal, intravascular device implantation, or the like may then be performed. For example, an imaging catheter may be inserted through the inner member and advanced past the distal end of the inner member to image the blood vessel or surrounding tissue. In the case of removing an embolus, such as in the treatment of an ischemic stroke, an embolus removal device may be inserted through the inner member, and advanced past the distal end of the inner member to grasp or otherwise capture the embolus, and remove the embolus from the blood vessel.

In an alternate embodiment of the balloon catheter, instead of the outer member being formed of a microporous material, the outer member has an impermeable wall (i.e., impermeable to air, contrast agent and saline) having one or more micro-holes drilled through the wall of the outer member. Thus, in this alternate embodiment, the balloon catheter includes an elongated, tubular outer member having a proximal portion, a distal portion, and an outer member lumen extending therebetween. The outer member has one or more micro-holes drilled through the wall of the outer member. The micro-holes are configured such that when a contrast agent is injected into the outer member lumen (i.e., into the inflation lumen), the micro-holes allow air to pass therethrough. In other words, air passes from the outer member lumen (more specifically, the inflation lumen) through the micro-holes to an exterior of the outer member. In addition, after allowing air to pass through, the micro-holes become clogged by the contrast agent thereby sealing the micro-holes from allowing contrast agent to pass through the micro-holes.

The alternate embodiment of the balloon catheter also has a flexible, elongated tubular inner member having a proximal portion, a distal portion, and an inner member lumen extending therebetween. The inner member lumen is in communication with a distal opening of the inner member. The inner member is at least partially disposed in the outer member lumen such that an outer surface of the inner member and an inner surface of the outer member together define an annular inflation lumen.

As with the exemplary embodiment, the balloon member is secured to the outer member. The balloon member can be secure to any suitable portion of the outer member, including but not limited to the distal portion. The proximal and distal ends of the balloon are secured to and circumferentially around an outer surface of the outer member such that an inner surface of the elastomeric member and an outer surface of the outer member define an inflatable balloon interior. The outer member also has one or more inflation passages through the wall of the outer member that form a fluid pathway between the annular inflation lumen and the balloon interior. The inflation passages may be holes in the through the wall of the outer member which fluidly connect the annular inflation lumen and the balloon interior.

The micro-holes of this alternate embodiment preferably have a nominal size diameter in the range of from 5 μm to 8 μm. This configuration of the micro-holes allows air to pass out through the micro-holes of the outer member when contrast agent is injected into the inflation lumen, and thereafter, the contrast agent clogs the micro-holes thereby sealing the micro-holes. In another aspect, the density of the micro-holes over the surface area of the outer member preferably does not exceed 16 micro-holes per $cm^2$ of surface area of the outer member. Alternatively, the density of the micro-holes over the surface area of the outer member preferably does not exceed 20 micro-holes per $cm^2$ of surface area of the outer member, or 10 micro-holes per $cm^2$ of surface area of the outer member, or 5 micro-holes per $cm^2$ of surface area of the outer member. This maximum density of the micro-holes over the surface area of the outer member helps ensure that the contrast agent will seal the micro-holes without allowing contrast agent (or an excessive amount of contrast agent) to leak out through the micro-holes.

As with the exemplary embodiment, the outer member of the alternate embodiment is preferably formed from a material, such as polyurethane, PEBAX™, VESTAMID™, a thermoplastic elastomer, and nylon, or other suitable material from which a flexible, elongated, tubular outer member may be formed, and micro-holes may be drilled through a wall of the tubular outer member. The micro-holes may be drilled using any suitable means, such as laser drilling, mechanical drilling, punching, etc., and are preferably positioned spaced apart along the outer member from the proximal portion to the distal portion of the outer member. For instance, the micro-holes can be arranged in a helical pattern along the outer member, or in a rectangular matrix, or other suitable pattern. The micro-holes preferably have a nominal hole area in the range of from 1 $μm^2$ to 210 $μm^2$. Similar to the nominal diameter, the nominal hole area allows air to pass out through the micro-holes of the outer member when contrast agent is injected into the inflation lumen, and the contrast agent clogs and seals the micro-holes after the air has been vented.

Another aspect of the disclosed inventions is directed to a method of purging air from the alternate embodiment of a balloon catheter. This air purging method is essentially the same as the method of purging air from the exemplary embodiment, except that air is purged out through the micro-holes, and the contrast agent seals the micro-holes, instead of the micropores.

Accordingly, embodiments described herein provide an innovative balloon and methods of using the same which allow for faster preparation and more effective purging of air within the catheter than prior balloon catheters.

BRIEF DESCRIPTION OF THE DRAWINGS

The foregoing, along with other and further embodiments and aspects of the disclosed inventions, with now be described in greater detail in the below detailed description, to be read in view of the accompanying figures, wherein like reference numerals refer to like elements and the description for like elements shall be applicable for all described embodiments wherever relevant.

DETAILED DESCRIPTION

Figure 1:
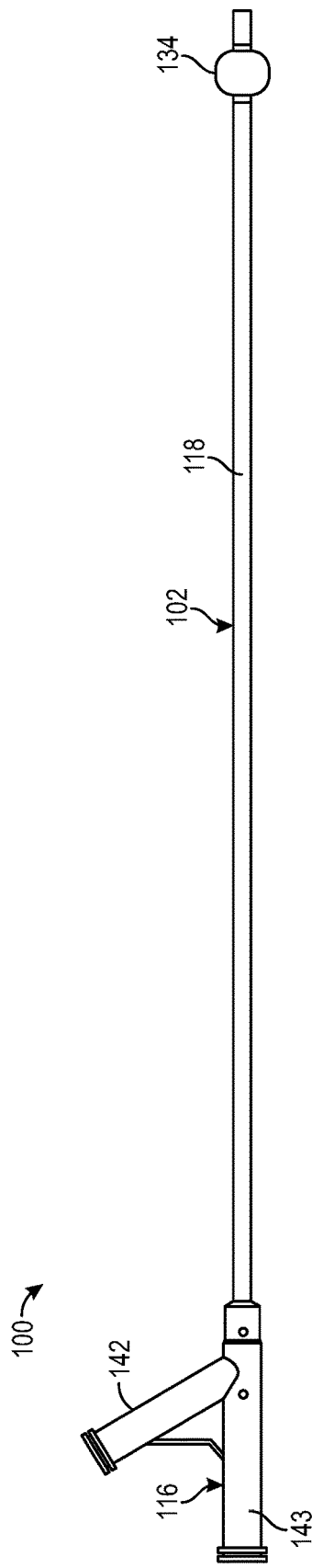
FIG. 1 is a side view of a balloon guide catheter in accordance with a first embodiment of the disclosed inventions.

FIGS. 1-5 illustrate a first embodiment of a balloon guide catheter 100 constructed in accordance with a first one embodiment of the disclosed inventions. The balloon guide catheter 100 is configured generally for performing a procedure within a vascular system, such as treating ischemic strokes and/or for blocking or restricting blood flow for other treatment or diagnostic purposes. In particular with respect to the disclosed inventions, the balloon guide catheter 100 is specially configured to allow for fast preparation of the catheter for performing a surgical procedure, including providing for fast and effective purging of air from the respective inflation lumen 121 and balloon interior 146, as described in greater detail below.

The balloon guide catheter 100 includes an elongated, flexible, tubular body 102 having a proximal portion 104, a distal portion 106 and an inner working lumen 108 extending therebetween. The working lumen 108 (defined in part by a hub 116 and in part by an inner member lumen 140) is in fluid communication with a distal opening 110 at a distal end 112 of the tubular body 102, and with a proximal opening 114 defined by a hub 116 (further described below) secured to the proximal portion 104 of the tubular body 102.

The tubular body 102 includes an elongated, flexible, tubular outer member 118 having a proximal portion 124 and a distal portion 126, and an outer member lumen 128 extending therebetween. The tubular body 102 also has an elongated, flexible, tubular inner member 120 coaxially disposed within the outer member lumen 128, such that the outer surface of the inner member 120 and the inner surface of the outer member 118 together define an annular inflation lumen 121.

The outer member 118 is formed of a microporous material such that the wall of the outer member 118 has micropores 122 along the entire wall of the outer member 118 extending from the proximal portion 124 to the distal portion 126. The micropores 122 are shown schematically in the figures, as the micropores 122 are quite small, and are distributed over the entire wall of the outer member 118. The microporous material has micropores 122 configured to allow air to pass through the wall of the outer member 118 when a contrast agent 123 is injected into the outer member lumen 128 (more specifically, into the inflation lumen 121) from the inflation lumen 121 out to the exterior of the outer member 118, as depicted by the arrows 132 in FIGS. 3 and 4. The configuration of the micropores 122 of the microporous material also provide for the micropores 122 to be clogged by the contrast agent 123 after the air is purged from the inflation lumen 121 and balloon member 134. In order to both purge the unwanted air and provide the contrast agent clogging effect, the microporous material has micropores 122 having a nominal pore size diameter ranging from 0.1 µm to 2.0 µm. In another way of defining the size of the microporous material, the micropores 122 have a nominal pore area size ranging from 0.079 µm² to 12.5 µm². In addition, the pore size diameter of the micropores 122 should not exceed 5 µm, in order to ensure that the micropores are properly clogged by the contrast agent after the air is purged. Thus, the microporous material may be any suitable material having properly configured micropores 122, including without limitation, TYVEK™ 3345, woven polymer, woven plastic, ePTFE, sintered plastic, sintered polymer, and GORETEX™ fabric membrane.

The inner member 120 has a proximal portion 136, a distal portion 138, and an inner member lumen 140 extending therebetween. The inner member 120 may each be made of a polymeric tube, or other suitable material, and may have one or more reinforcing members (not shown) to provide reinforced and/or stiffened portions. For example, a coil, braid, ribbon, hypotube, or other structural member may be disposed on the inside, on the outside, and/or embedded within a wall of the inner member 120. Such reinforcing members may be made of any suitable material, such as a super-elastic alloy or shape-memory material to provide a specific shape to the reinforced portion of the tubular body 102 under certain conditions.

As mentioned above, the balloon guide catheter 100 further includes a hub 116 secured to the proximal portion 104 of the tubular body 102 (i.e., to each of the inner and outer members 118 and 120). The hub 116 defines the proximal end opening 114 of the working lumen 108. The hub 116 includes a balloon inflation port 142 in fluid communication with the proximal end of the inflation lumen 121. The balloon inflation port 142 is configured to be connected to an inflation syringe 152 (not drawn to scale) (see FIGS. 3-5) or other source of pressurized inflation fluid for purging air from the balloon guide catheter 100 when prepping the catheter 100 for a surgical procedure. For example, the balloon inflation port 142 may have a female Luer lock (not shown) for attaching the inflation syringe 152 or other fluid source, having a mating male Luer lock (not shown).

The inflation lumen 121 extends along the length of the outer member 118 from the balloon inflation port 142 to an inflatable balloon interior 146 (best seen in FIG. 5 in which the balloon interior 36) of a balloon member 134 secured to the outer member 118. In the illustrated first embodiment, the outer member 118 and inner member 120 are connected at the distal portion 126 of the outer member 118 thereby forming the distal end of the inflation lumen 121. The outer member 118 and inner member 120 may also be bonded to each other at one or more other locations (not shown) distal of the hub 116. However, such bonds are not fully circumferential so as to ensure the inflation lumen 121 is continuous from the inflation port 142 to the balloon interior. Alternative to the annular inflation lumen 121, the inflation lumen 121 may be one or more channels, conduits, tubes, etc., formed in the wall of the outer member 118. Alternatively, the inflation lumen 121 may be one or more channels, conduits, tubes, etc., formed in, or attached to, the wall of the outer member 118.

The hub 116 also has a working lumen port 143 which is in fluid communication with the working lumen 108. The working lumen port 143 is configured to be connected to a source of purging fluid (e.g., saline) to purge air from the working lumen 108. A source of flushing fluid (e.g., saline) and/or a source of fluid medication may be connected to the working lumen port 143 during a surgical procedure with the balloon guide catheter 100 in order to flush the target a target site within a vascular system, and/or to deliver medication to the target site. The working lumen port 143 may have a female Luer lock (not shown) for attaching a syringe 68 or other fluid source having a mating male Luer lock, such as a syringe 155 (see FIG. 5).

In the illustrated embodiment, the balloon member 134 is secured to the distal portion 126 of the outer member 118. However, the balloon member 134 may be secured to any suitable location on the outer member 118, including proximal to the distal portion 126, or in the middle portion of the outer member 118, etc. The balloon member 134 is typically elastomeric, but may also be non-elastomeric. The balloon member 134 may be transparent, or translucent (i.e., semi-transparent), so that the balloon member 134 can be visually inspected for air bubbles while purging air from the catheter 100, as described herein. The proximal end 148 and distal end 150 of the balloon member 134 are secured to, and circumferentially around, the outer surface of the outer member 118. In this way, the inner surface of the balloon member 134 and the outer surface of the outer member 118 form the inflatable balloon interior 146. The outer member 118 and inner member 120 may be bonded to each other at one or more locations (not shown) distal of the hub 19. However, such bonds are not fully circumferential so as to ensure the inflation lumen 121 is continuous from the inflation port 142 to the balloon interior 146.

The outer member 118 has one or more balloon inflation passages 156 through the wall of the outer member 118 within the balloon interior. The inflation passages 156 form a fluid pathway through the wall of the outer member between the inflation lumen 121 and the inflatable balloon interior 146. In the illustrated embodiment, the outer member 118 has 4 inflation passages 156, wherein the inflation passages 156 are spaced longitudinally along the outer member 118, and circumferentially around the outer member 118 (in the illustrated embodiment, the inflation passages are spaced 180° around the circumference of the outer member 118). The balloon guide catheter 100 may have any suitable number of inflation passages 156, such as between 1 and 10 inflation passages 156.

Figure 2:
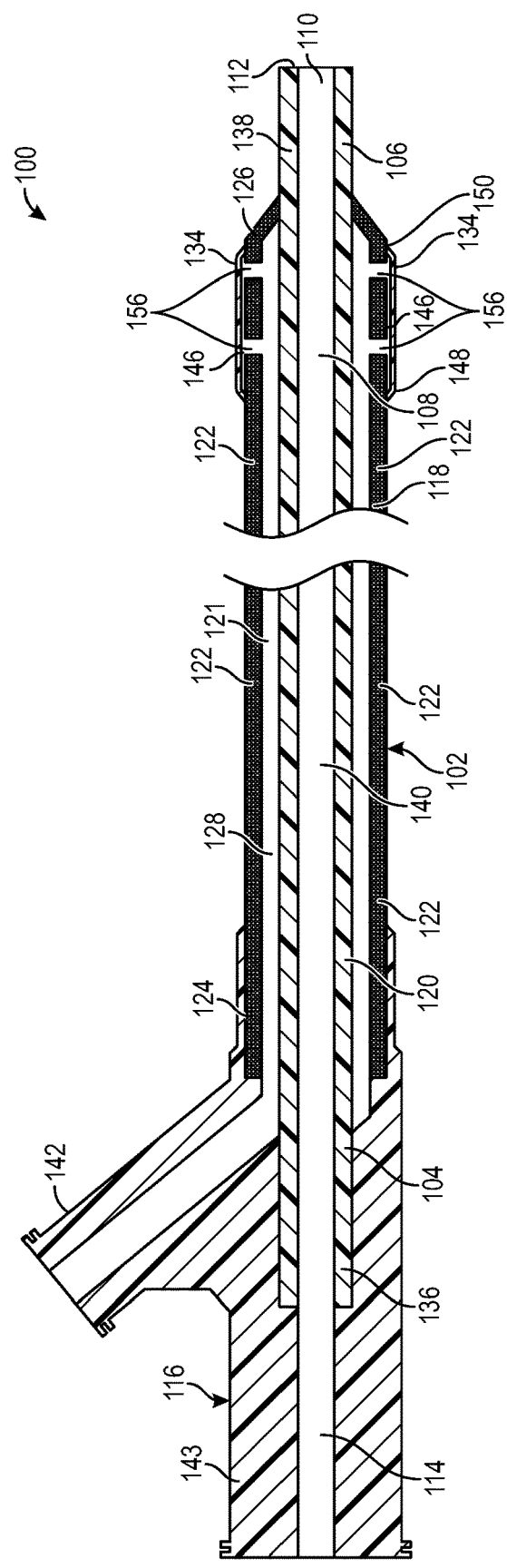
FIG. 2 is a side, cross-sectional view of the balloon guide catheter of FIG. 1.
Figure 3:
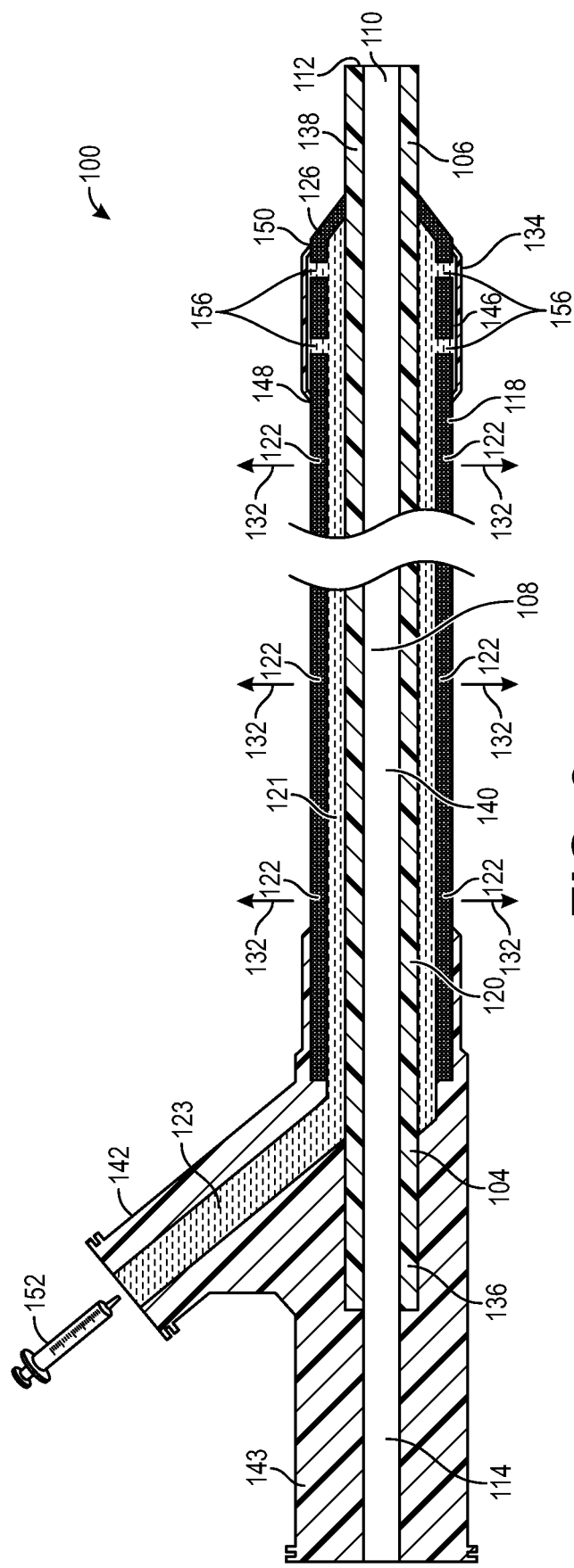
FIG. 3 depicts the balloon guide catheter of FIG. 1 being purged of air by injecting a contrast agent into the inflation lumen and air passing through the micropores of the outer member.

A method of purging air from the balloon guide catheter 100 in order to prepare ("prep") the catheter 100 for use in a medical procedure, will now be described with reference to FIGS. 1-6. As shown in FIG. 2, the balloon guide catheter 100 is first provided without any liquid in the catheter 100, such that there is air in the inflation lumen 121 and the working lumen 108. In order to prep the balloon guide catheter 100 to be used in a surgical procedure, the air is purged from the catheter 100, including the inflation lumen 121 and the working lumen 108. The method will described with purging the inflation lumen 121 first, and the working lumen 108 thereafter, but the method can also be performed in the reverse order, or even purging both simultaneously.

Referring to FIG. 2, in order to purge air from the inflation lumen 121, a source 152 of contrast agent 123 is attached to the inflation port 142. In the illustrated embodiment, the source of contrast agent 123 is the inflation syringe 152 filled with contrast agent 123. The syringe 152 may have a male Luer lock which mates with the female Luer lock of the inflation port 142. The syringe 152 is used to inject the contrast agent 123 into the inflation port 142, into the inflation lumen 121 and into the balloon member 134. As the inflation lumen 121 is filled with contrast agent 123, the air in the inflation port 142, inflation lumen 121 and the balloon member 134 is forced out through the micropores 122 to the exterior of the outer member 118 as indicated by the arrows 132. The syringe 152 is used to maintain a positive pressure of contrast agent 123 in the inflation port 142, inflation lumen 121 and balloon member 134.

Figure 4:
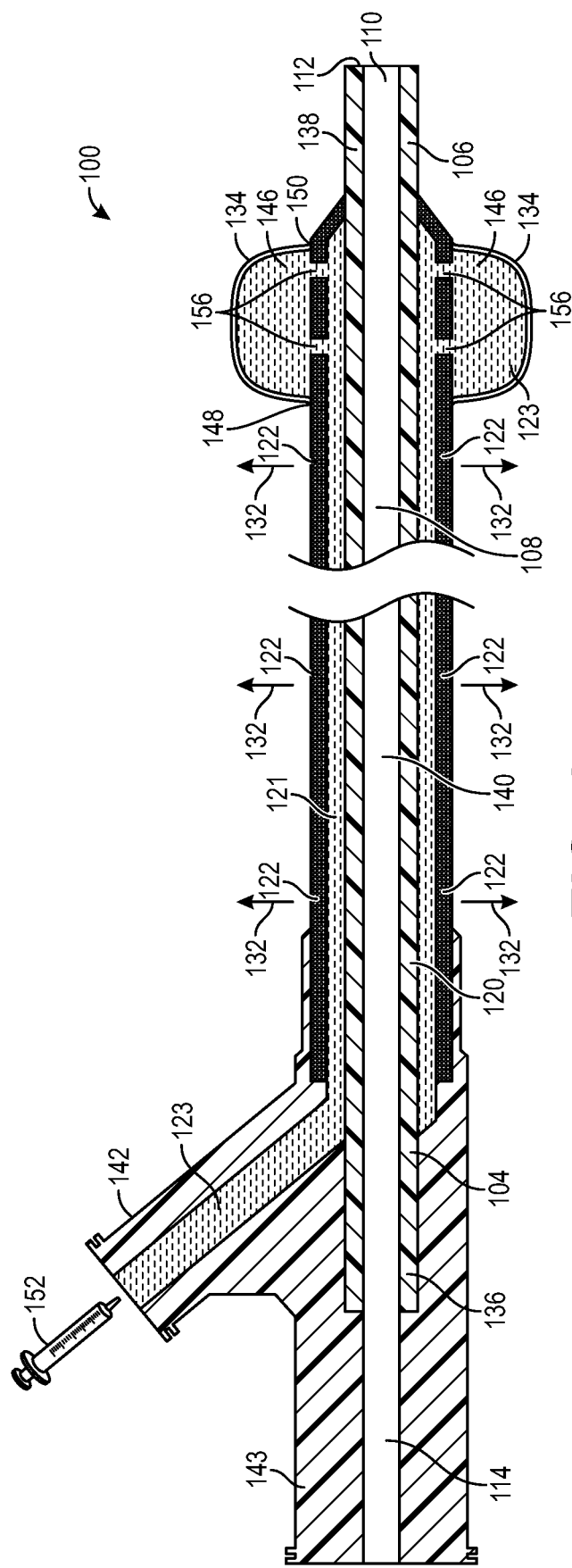
FIG. 4 depicts the balloon guide catheter of FIG. 1 being purged of air with the balloon member inflated, and air passing through the micropores of the outer member.

As shown in FIG. 4, after the inflation port 142, inflation lumen 121 and balloon member 134 are filled with contrast agent 123, additional contrast agent 123 is injected into the inflation port 142 using the syringe 152 which inflates the balloon member 134. Air continues to be purged out of through the micropores 122. The balloon guide catheter 100 is then manipulated to position the outer member 118 above the balloon member 134 (in other words, positioning the balloon member 134 below the remainder of the balloon guide catheter 100 proximal to the balloon member 134) so that any air remaining in the balloon member 134 is forced into the outer member 118 and then passes out through the micropores 122 of the outer member 118. The positioning of the balloon 134 below the outer member 118 may be also be done at any other time during the purging of air from the inflation lumen 121 and balloon member 134, such as before initially injecting contrast agent into the inflation port 142, inflation lumen 121 and balloon 134, or just prior to inflating the balloon member 134, etc.

With the balloon member 134 inflated, the balloon member 134 is visually inspected for air (e.g., inspecting for air bubbles), by a user prepping the balloon guide catheter 100. The user determines whether any air is remaining in the balloon member 134. The balloon member 134 may also be visually inspected for any leaks. If the balloon member 134 has leaks, the balloon guide catheter 100 may be rejected and replaced. If the balloon member 134 is confirmed to have no leaks, then the method of prepping the balloon guide catheter 100 may proceed.

Figure 5:
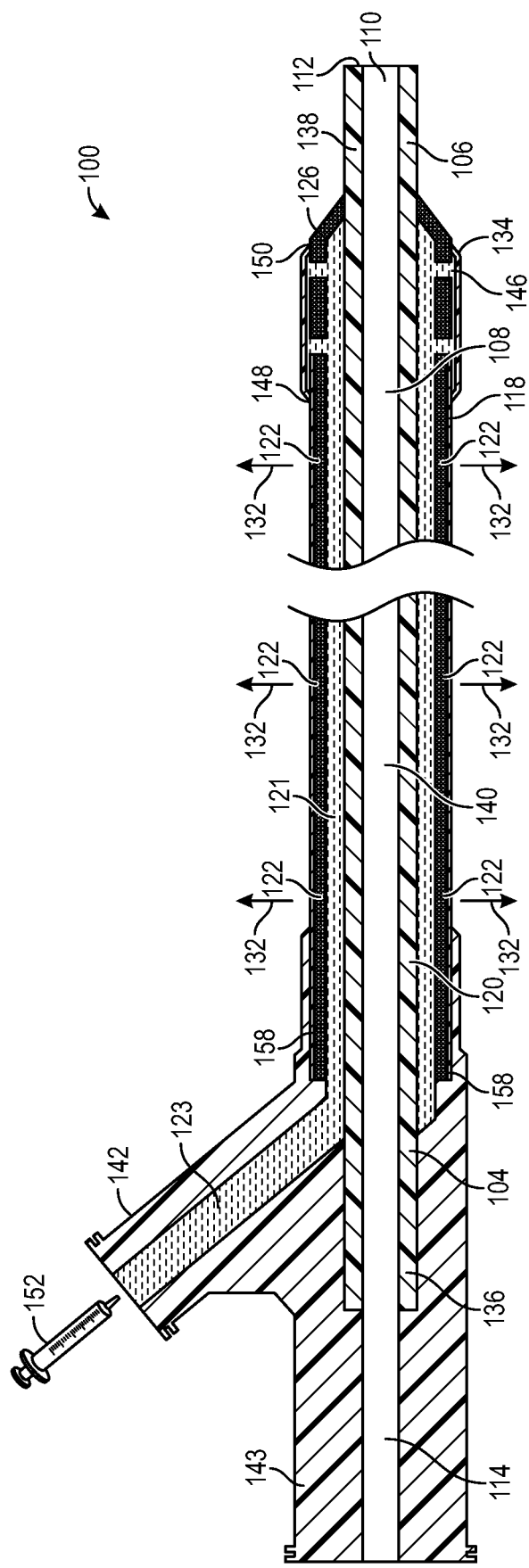
FIG. 5 depicts balloon guide catheter of FIG. 1 after the micropores are clogged and sealed by contrast agent and the balloon member has been deflated.

As the air is being forced out through the micropores 122 of the outer member 118, the contrast agent 123 clogs the micropores 122. As shown in FIG. 5, the clogged micropores 158 are depicted by the lines 158. The clogged micropores 158 are sealed by the contrast agent 123 from allowing contrast agent 123 to pass through the micropores 122. As described herein, the micropores 122 are configured to allow air to be purged out through micropores 122 from the inflation lumen 121, and thereafter, are clogged and sealed by the contrast agent 123. Also, as shown in FIG. 5, after the air is purged from the inflation lumen 121 and balloon member 134, the balloon member 134 is deflated so that it can be inserted into a vascular system uninflated. The air is now purged from the inflation port 142, inflation lumen 121 and balloon member 134, and the balloon member 134 is deflated.

Figure 6:
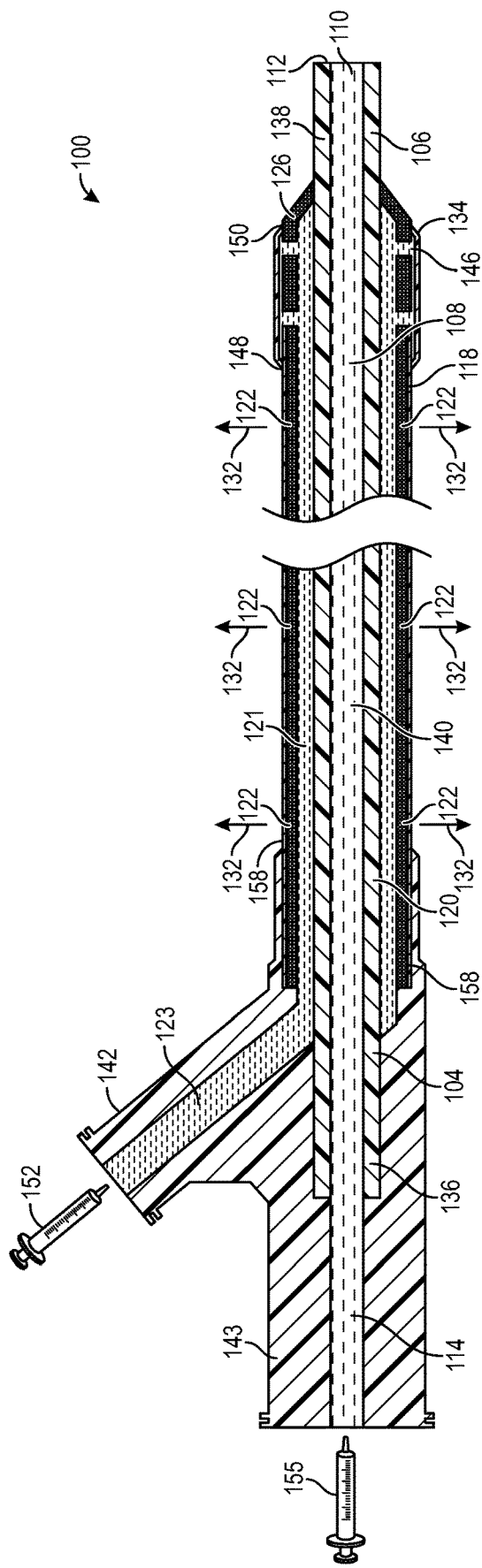
FIG. 6 depicts the balloon guide catheter of FIG. 1 with the inner member lumen being purged of air by injecting saline into the inner member lumen.
Figure 7:
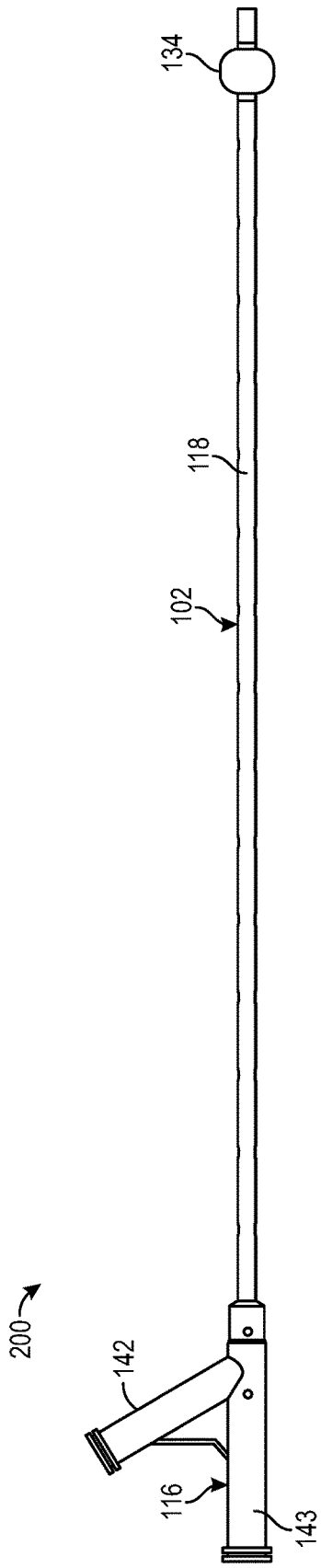
FIG. 7 is a side view of a balloon guide catheter in accordance with a second embodiment of the disclosed inventions.

As depicted in FIG. 6, prepping the balloon guide catheter 100 may also include purging air from working lumen 108, including inner member lumen 140 of the inner member 120 and the working lumen port 143. A source of flushing fluid, typically a purging syringe 155 filled with saline 160, is connected to the working lumen port 143. The syringe 155 may have a male Luer lock which mates with the female Luer lock of the working lumen port 143. The syringe 155 is used to inject the saline 160 into the working lumen 108 thereby purging air from the working lumen 108, including the inner member lumen 140 of the inner member 120 and the inflation port 142. The user may visually inspect the saline 160 exiting the distal opening 110 of the inner member lumen 140 for air bubbles, and when there are no air bubbles, the working lumen 108 is purged of air. The working lumen 108 remains filled with saline 160 in the prepped balloon guide catheter 100 (e.g., surface tension retains the saline 160 within the working lumen 108).

The balloon guide catheter 100 is now purged of air, and fully prepped for use in a surgical procedure.

The method of using the prepped balloon guide catheter 100 in a medical procedure may include any suitable use of the balloon guide catheter 100. In one exemplary method, the balloon guide catheter 100 is inserted into the vascular system of the patient. For example, the balloon guide catheter 100 may be inserted through an entry incision into an entry blood vessel, such as the inferior vena cava or femoral artery near the groin. The balloon guide catheter 100, including the inner member 120, outer member 118, and balloon member 134, are advanced through the vascular system to position the balloon 134 at a treatment site. The contrast agent 123 allows the user to track the position of the balloon guide catheter 100 using a suitable medical imaging device, such as a radiography machine, MRI, etc. The inner member 120 and outer member 118 may be advanced simultaneously, or separately, and at the same rate or different rates. In the illustrated embodiment, the inner member 120 and outer member 118 are connected at the distal portion 126 of the outer member 118 so they are advanced simultaneously.

With the balloon member 134 positioned at the treatment site, the balloon member 134 is inflated by injecting contrast agent into the inflation lumen 121 using the inflation syringe 152 (or other suitable source of inflation fluid), thereby increasing the pressure of contrast agent 123 in the inflation lumen 121 and balloon member 134. The balloon member 134 may be inflated within the blood vessel such that the balloon member 134 seals the blood vessel. This isolates the blood vessel downstream of the balloon member 134 from the flow of blood. The syringe 152 may also be used to inject saline 160 to the treatment site, to flush the treatment site. A syringe 152 of medication or other therapeutic substance may be used to inject the medication or other substance to the treatment site. Alternatively, or in addition, a treatment procedure, such as imaging, embolus removal, intravascular device implantation, or the like may be performed. For example, an imaging catheter may be inserted through the working lumen 108, including the inner member lumen 140, and advanced past the distal end of the inner member 120 to image the blood vessel or surrounding tissue. In the case of removing an embolus, such as in the treatment of an ischemic stroke, an embolus removal device may be inserted through the inner member lumen 140, and advanced past the distal end 112 of the inner member 118 to grasp or otherwise capture the embolus, and remove the embolus from the blood vessel.

Turning to FIGS. 7-12, a second embodiment of a balloon guide catheter 200 is illustrated. The balloon guide catheter 200 is also specially configured to allow for fast preparation of the catheter for performing a surgical procedure, including providing for fast and effective purging of air from the respective inflation lumen 121 and balloon interior 146, as described herein. The balloon guide catheter 200 is substantially the same as the balloon guide catheter 100, except that instead of the outer member 118 being formed of a microporous material, the outer member has an impermeable wall having one or more micro-holes 202 drilled through the wall of the outer member 118.

Accordingly, the outer member 118 has one or more micro-holes 202 drilled through the wall of the outer member 118. The micro-holes 202 are configured such that when the contrast agent 123 is injected into the inflation lumen 121 using the syringe 152, the micro-holes 202 allow air to pass therethrough to the exterior of the outer member 118. In other words, air passes from the outer member lumen (more specifically, the inflation lumen) through the micro-holes to an exterior of the outer member. In addition, after allowing air to pass through, the micro-holes become clogged by the contrast agent thereby sealing the micro-holes from allowing contrast agent to pass through the micro-holes.

The outer member 118 may be formed from any suitable material, such as polyurethane, PEBAX™, VESTAMID™, a thermoplastic elastomer, and nylon, or other suitable material from which a flexible, elongated, tubular outer member may be formed, and micro-holes may be drilled through a wall of the tubular outer member. The micro-holes 202 may be drilled using any suitable means, such as laser drilling, mechanical drilling, punching, etc.

In order to both purge the unwanted air and provide the contrast agent clogging effect, the micro-holes 202 have a nominal size diameter in the range of from 5 µm to 8 µm. This configuration of the micro-holes 202 allows air to pass out through the micro-holes 202 of the outer member 118 when contrast agent 123 is injected into the inflation lumen 121, and thereafter, the contrast agent 123 clogs the micro-holes 202 thereby sealing the micro-holes from allowing contrast agent 123 to leak out. Alternatively, or in addition, the size of the micro-holes 202 may be defined in term of area. For instance, the micro-holes 202 have a nominal hole area in the range of from 1 µm$^2$ to 210 µm$^2$. Similar to the nominal diameter, the nominal hole area allows air to pass out through the micro-holes 202 of the outer member 118 when contrast agent is injected into the inflation lumen 121, and the contrast agent 123 clogs and seals the micro-holes 202 after the air has been purged.

The density of the micro-holes 202 over the surface area of the outer member 118 may have a maximum density in order to ensure that the contrast agent 123 will seal the micro-holes 202 without allowing contrast agent 118 (or an excessive amount of contrast agent) to leak out through the micro-holes 202. The density of the micro-holes 202 over the surface area of the outer member 118 preferably does not exceed 16 micro-holes per cm$^2$ of surface area of the outer member 118. Alternatively, the density of the micro-holes 202 over the surface area of the outer member 118 does not exceed 20 micro-holes per cm$^2$ of surface area of the outer member 118, or 10 micro-holes per cm$^2$ of surface area of the outer member 118, or 5 micro-holes 202 per cm$^2$ of surface area of the outer member 118.

The micro-holes 202 are spaced apart along the outer member 118 from the proximal portion 124 to the distal portion 126 of the outer member 118. The micro-holes 202 may be arranged in a pattern along the outer member 118, such as one or more helical patterns along the outer member 118, or in a rectangular matrix, or other suitable pattern.

Figure 8:
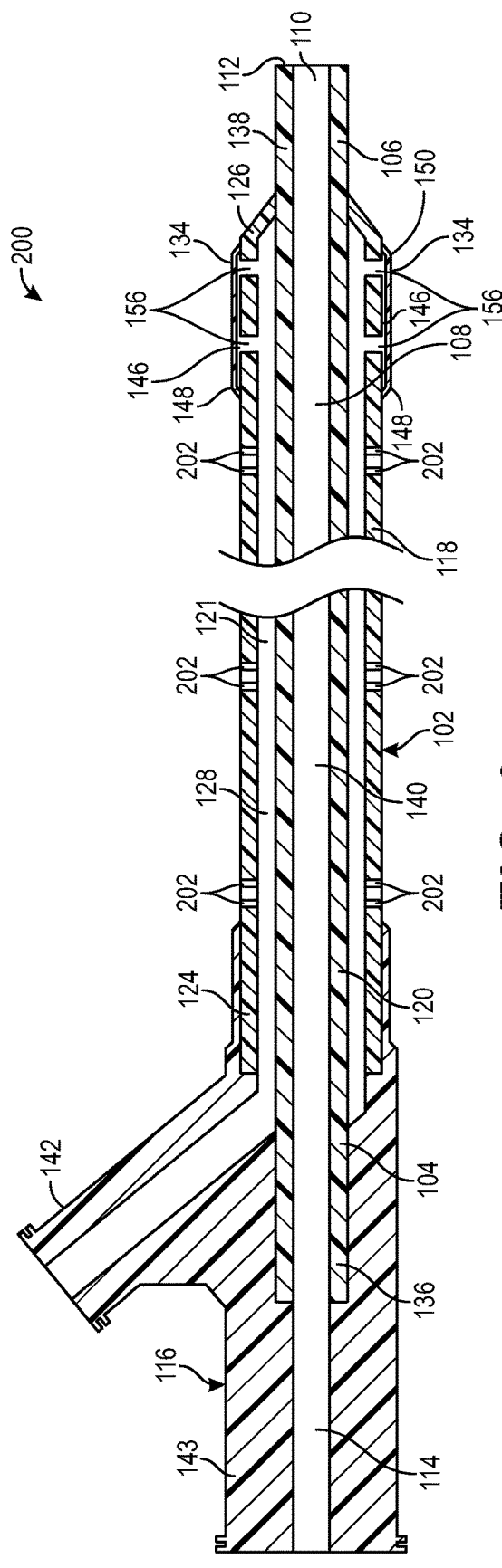
FIG. 8 is a side, cross-sectional view of the balloon guide catheter of FIG. 7.

As shown in FIGS. 7-12, the method of prepping balloon guide catheter 200 for use in a surgical procedure is substantially the same as the method of prepping the balloon guide catheter 100. As shown in FIG. 8, the balloon guide catheter 200 is first provided without any liquid in the catheter 200, such that there is air in the inflation lumen 121 and the working lumen 108. In order to prep the balloon guide catheter 200 to be used in a surgical procedure, the air needs to be purged from the catheter 200, including the inflation lumen 121 and the working lumen 108. Same as the catheter 100, the method will described with purging the inflation lumen 121 first, and the working lumen 108 thereafter, but the method can also be performed in the reverse order, or even purging both simultaneously.

Figure 9:
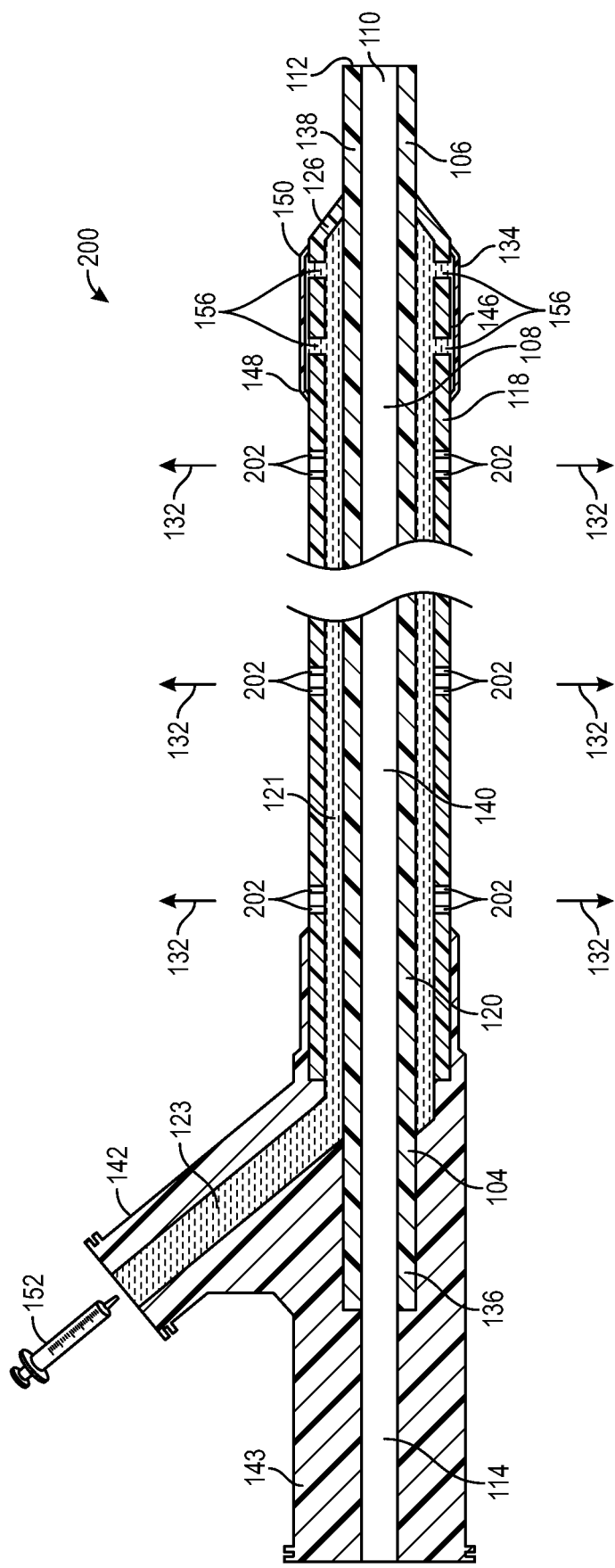
FIG. 9 depicts the balloon guide catheter of FIG. 7 being purged of air by injecting a contrast agent into the inflation lumen and air passing through the micro-holes of the outer member.

Turning to FIG. 9, in order to purge air from the inflation lumen 121, a source 152 of contrast agent 123 is attached to the inflation port 142. Again, the source of contrast agent 123 is the inflation syringe 152 filled with contrast agent 123. The syringe 152 may have a male Luer lock which mates with the female Luer lock of the inflation port 142. The syringe 152 is used to inject the contrast agent 123 into the inflation port 142, into the inflation lumen 121 and into the balloon member 134. As the inflation lumen 121 is filled with contrast agent 123, the air in the inflation port 142, inflation lumen 121 and the balloon member 134 is forced out through the micro-holes 202 to the exterior of the outer member 118 as indicated by the arrows 132. The syringe 152 is used to maintain a positive pressure of contrast agent 123 in the inflation port 142, inflation lumen 121 and balloon member 134.

Figure 10:
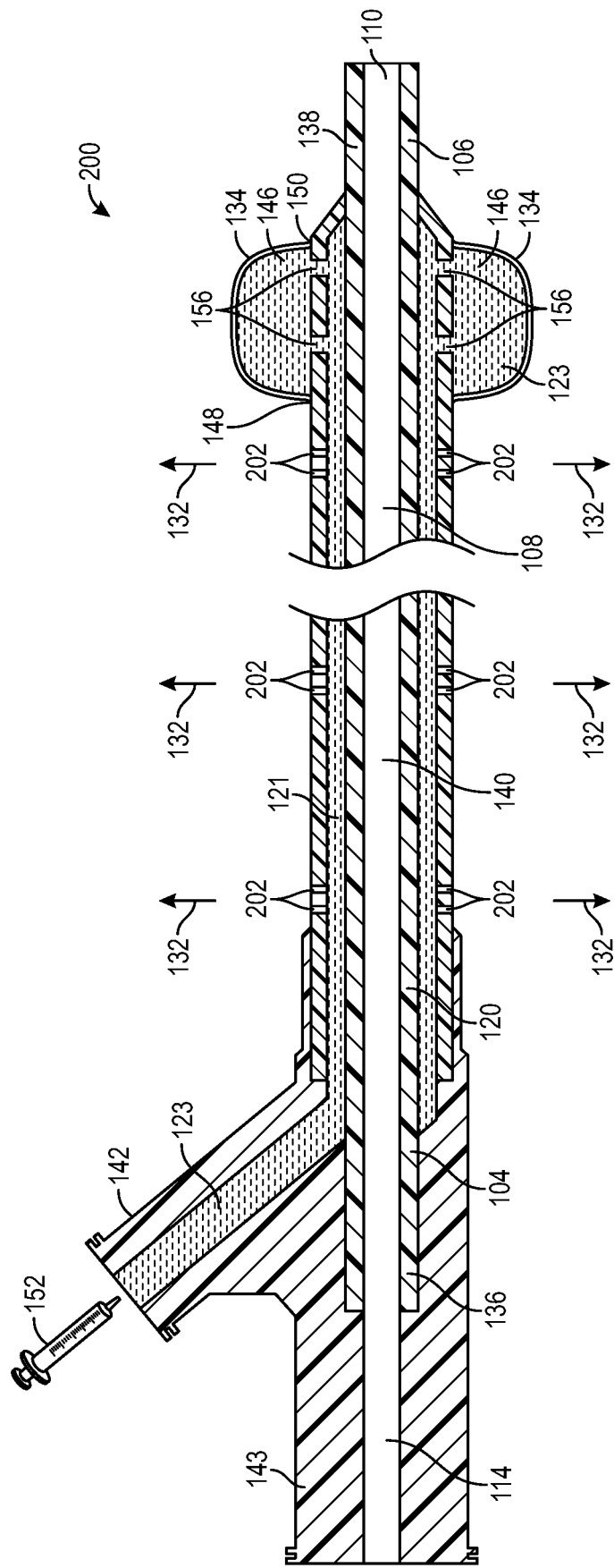
FIG. 10 depicts the balloon guide catheter of FIG. 7 being purged of air with the balloon member inflated, and air passing through the micro-holes of the outer member.

As shown in FIG. 10, after the inflation port 142, inflation lumen 121 and balloon member 134 are filled with contrast agent 123, additional contrast agent 123 is injected into the inflation port 142 using the syringe 152 which inflates the balloon member 134. Air continues to be purged out of through the micro-holes 202. The balloon guide catheter 200 is then manipulated to position the outer member 118 above the balloon member 134 (in other words, positioning the balloon member 134 below the remainder of the balloon guide catheter 200 proximal to the balloon member 134) so that any air remaining in the balloon member 134 is forced into the outer member 118 and then passes out through the micro-holes 202 of the outer member 118. The positioning of the balloon 134 below the outer member 118 may be also be done at any other time during the purging of air from the inflation lumen 121 and balloon member 134, such as before initially injecting contrast agent into the inflation port 142, inflation lumen 121 and balloon 134, or just prior to inflating the balloon member 134, etc.

With the balloon member 134 inflated, the balloon member 134 is visually inspected for air (e.g., inspecting for air bubbles), by a user prepping the balloon guide catheter 200. The user determines whether any air is remaining in the balloon member 134. The balloon member 134 may also be visually inspected for any leaks. If the balloon member 134 has leaks, the balloon guide catheter 200 may be rejected and replaced. If the balloon member 134 is confirmed to have no leaks, then the method of prepping the balloon guide catheter 200 may proceed.

Figure 11:
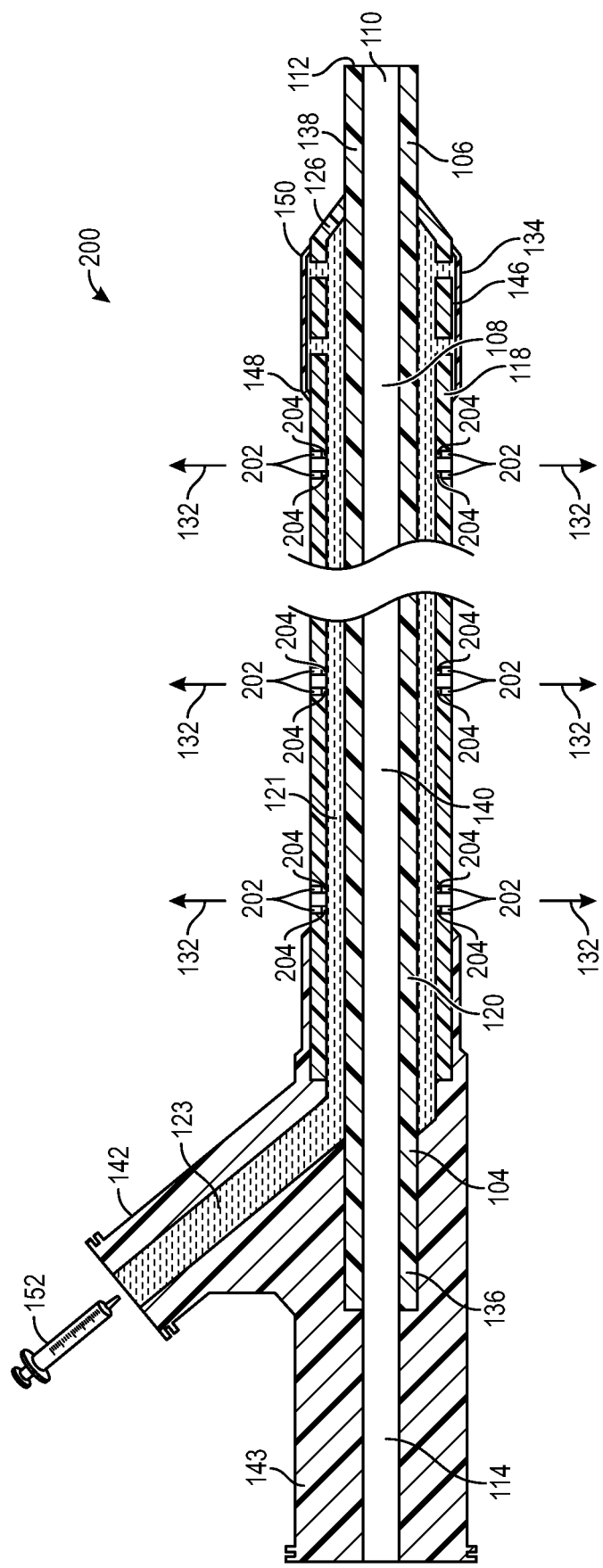
FIG. 11 depicts balloon guide catheter of FIG. 7 after the micro-holes are clogged and sealed by contrast agent and the balloon member has been deflated.
Figure 12:
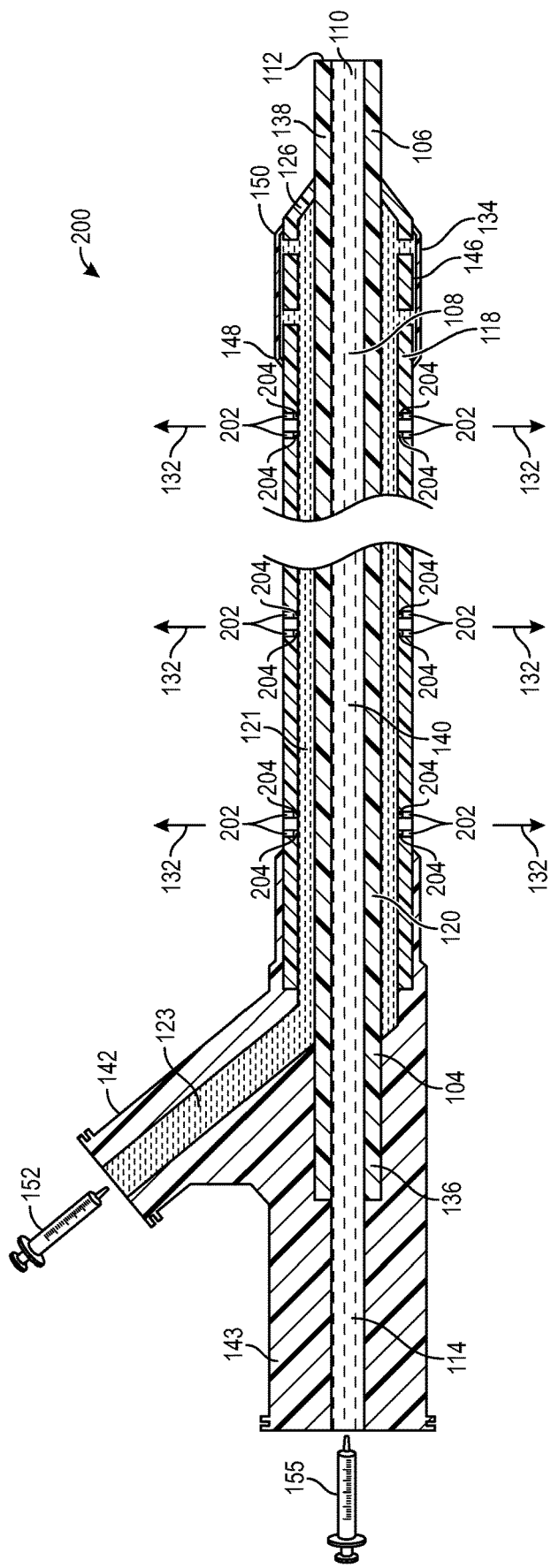
FIG. 12 depicts the balloon guide catheter of FIG. 7 with the inner member lumen being purged of air by injecting saline into the inner member lumen.
Figure 13A:
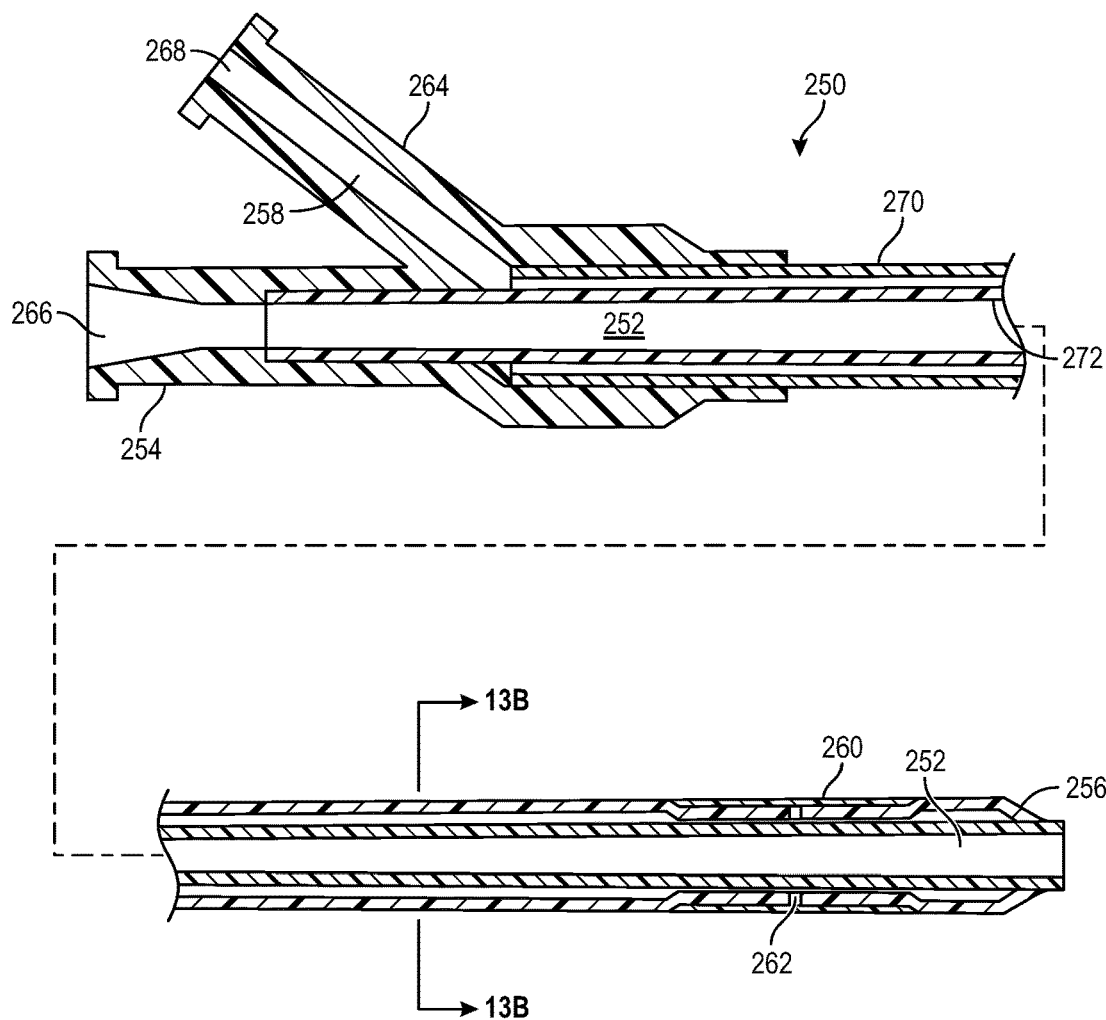
FIGS. 13A and 13B depict a prior art balloon guide catheter, as disclosed in the U.S. Pat. No. 6,638,245.
Figure 13B:
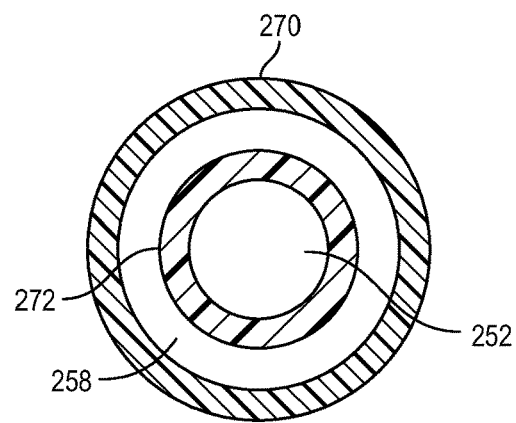

As the air is being forced out through the micro-holes 202 of the outer member 118, the contrast agent 123 clogs the micro-holes 202. As shown in FIG. 11, the micro-holes 202 are sealed by the plugs 204 formed by the contrast agent 123. The clogged micro-holes 202 are sealed by the contrast agent 123 from allowing contrast agent 123 to pass through the micro-holes 202. As described herein, the micro-holes 202 are configured to allow air to be purged out through micro-holes 202 from the inflation lumen 121, and thereafter, are clogged and sealed by the contrast agent 123. Also, as shown in FIG. 11, after the air is purged from the inflation lumen 121 and balloon member 134, the balloon member 134 is deflated so that it can be inserted into a vascular system uninflated. The air is now purged from the inflation port 142, inflation lumen 121 and balloon member 134, and the balloon member 134 is deflated.

Prepping the balloon guide catheter 200 may also include purging air from the working lumen 108, including inner member lumen 140 of the inner member 120 and the working lumen port 143. The purging syringe 155 filled with saline 160 is connected to the working lumen port 143. The syringe 155 may have a male Luer lock which mates with the female Luer lock of the working lumen port 143. The syringe 155 is used to inject the saline 160 into the working lumen 108 thereby purging air from the working lumen 108, including the inner member lumen 140 of the inner member 120 and the inflation port 142. The user may visually inspect the saline 160 exiting the distal opening 110 of the inner member lumen 140 for air bubbles, and when there are no air bubbles, the working lumen 108 is purged of air. The working lumen 108 remains filled with saline 160 in the prepped balloon guide catheter 200 (e.g., surface tension retains the saline 160 within the working lumen 108).

The balloon guide catheter 200 is now purged of air, and fully prepped for use in a surgical procedure.

The method of using the prepped balloon guide catheter 200 in a medical procedure is substantially the same as for prepped balloon guide catheter 100, as described herein.

Although particular embodiments have been shown and described, it is to be understood that the above description is not intended to limit the scope of these embodiments. While embodiments and variations of the many aspects of the invention have been disclosed and described herein, such disclosure is provided for purposes of explanation and illustration only. Thus, various changes and modifications may be made without departing from the scope of the claims. For example, not all of the components described in the embodiments are necessary, and the invention may include any suitable combinations of the described components, and the general shapes and relative sizes of the components of the invention may be modified. Accordingly, embodiments are intended to exemplify alternatives, modifications, and equivalents that may fall within the scope of the claims. The invention, therefore, should not be limited, except to the following claims, and their equivalents.

What is claimed is:

1. A balloon catheter, comprising:
an elongated, tubular outer member having a proximal portion, a distal portion, and an outer member lumen extending therebetween, the tubular outer member formed of a microporous material such that a wall of the outer member has micropores that are configured such that when a contrast agent is injected into the outer member lumen, the micropores allow air to pass therethrough and thereafter become clogged by the contrast agent and thereby sealing micropores from allowing contrast agent to pass through the micropores;
a tubular inner member having a proximal portion, a distal portion, and an inner member lumen extending therebetween, wherein the inner member lumen is in communication with a distal opening of the inner member, the inner member being at least partially disposed in the outer member lumen such that an outer surface of the inner member and an inner surface of the outer member together define an annular inflation lumen;
a balloon member having respective proximal and distal ends secured to and circumferentially around an outer surface of the distal portion of the outer member such that an inner surface of the balloon member and the outer surface of the outer member together define an inflatable balloon interior; and
the outer member having one or more inflation passages through the wall of the outer member that form a fluid pathway between the annular inflation lumen and the balloon interior.

2. The balloon catheter of claim 1, wherein the microporous material has micropores having a nominal pore size diameter in the range of from 0.1 μm to 2 μm.

3. The balloon catheter of claim 1, wherein the pore size diameter of the micropores does not exceed 5 μm.

4. The balloon catheter of claim 1, wherein the microporous material is selected from the group consisting of woven polymer, woven plastic, ePTFE, sintered plastic, and sintered polymer.

5. The balloon catheter of claim 1, wherein the micropores extend from the proximal portion to the distal portion of the outer member.

6. The balloon catheter of claim 1, wherein the wherein the microporous material has micropores having a nominal pore area size in the range of from 0.079 μm$^2$ to 12.5 μm$^2$.

7. A balloon catheter, comprising:
an elongated, tubular outer member having a proximal portion, a distal portion, and an outer member lumen extending therebetween, the tubular outer member having one or more micro-holes drilled through a wall of the outer member, the one or more micro-holes configured such that when a contrast agent is injected into the outer member lumen, the micro-holes allow air to pass therethrough and thereafter become clogged by the contrast agent and thereby seal the one or more holes from allowing contrast agent to pass through the micro-holes;
a tubular inner member having a proximal portion, a distal portion, and an inner member lumen extending therebetween, wherein the inner member lumen is in communication with a distal opening of the inner member, the inner member being at least partially disposed in the outer member lumen such that an outer surface of the inner member and an inner surface of the outer member together define an annular inflation lumen;
a balloon member having respective proximal and distal ends secured to and circumferentially around an outer surface of the distal portion of the outer member such that an inner surface of the balloon member and the outer surface of the outer member together define an inflatable balloon interior; and
the outer member having one or more inflation passages through the wall of the outer member that form a fluid pathway between the annular inflation lumen and the balloon interior.

8. The balloon catheter of claim 7, wherein the micro-holes have a nominal size diameter in the range of from 5 μm to 8 μm.

9. The balloon catheter of claim 7, wherein the outer member is formed from a material selected from the group consisting of polyurethane, a thermoplastic elastomer, and nylon.

10. The balloon catheter of claim 7, wherein the micro-holes extend from the proximal portion to the distal portion of the outer member.

11. The balloon catheter of claim 7, wherein the wherein the micro-holes have a nominal hole area in the range of from 1 μm² to 210 μm².

12. A method of purging air from the balloon catheter of claim 1, comprising:
injecting a contrast agent into the annular inflation lumen, through the inflation passages and into the balloon thereby purging air from inflation lumen and the balloon interior out through the micro-holes of the outer member; and
maintaining a positive pressure of contrast agent in the annular inflation lumen such that the contrast agent seals the micropores of the outer member.

13. The method of claim 12, wherein the contrast agent is injected into the annular inflation lumen with sufficient pressure to inflate the balloon, and wherein the method further comprises:
positioning the balloon catheter with the tubular outer member elevated above the balloon such that air trapped in the balloon is forced into the tubular outer member and passes out of the tubular member through the micropores of the outer member.

14. The method of claim 13, further comprising:
inspecting the balloon for air bubbles while the balloon is inflated with contrast agent; and
determining that any air bubbles in the balloon are purged from balloon;
after determining that any air bubbles in the balloon are purged from balloon, deflating the balloon by reducing the pressure of the contrast agent within the inflation lumen and balloon interior.

15. A method of purging air from the balloon catheter of claim 7, comprising:
injecting a contrast agent into the annular inflation lumen, through the inflation passages and into the balloon thereby purging air from inflation lumen and the balloon interior out through the micro-holes of the outer member; and
maintaining a positive pressure of contrast agent in the annular inflation lumen such that the contrast agent seals the micro-holes of the outer member.

16. The method of claim 15, wherein the contrast agent is injected into the annular inflation lumen with sufficient pressure to inflate the balloon, and wherein the method further comprises:
positioning the balloon catheter with the tubular outer member elevated above the balloon such that air trapped in the balloon is forced into the tubular outer member and passes out of the tubular member through the micro-holes of the outer member.

17. The method of claim 16, further comprising:
inspecting the balloon for air bubbles while the balloon is inflated with contrast agent; and
determining that any air bubbles in the balloon are purged from balloon;
after determining that any air bubbles in the balloon are purged from balloon, deflating the balloon by reducing the pressure of the contrast agent within the inflation lumen and balloon interior.

* * * * *